(12) United States Patent
Henderson

(10) Patent No.: US 11,771,503 B1
(45) Date of Patent: Oct. 3, 2023

(54) SCREEN-MOUNTED TRAJECTORY AND AIMING GUIDE FOR USE WITH FLUOROSCOPY

(71) Applicant: Dartmouth-Hitchcock Clinic, Lebanon, NH (US)

(72) Inventor: Eric R. Henderson, Lebanon, NH (US)

(73) Assignee: Dartmouth-Hitchcock Clinic, Lebanon, NH (US)

(*) Notice: Subject to any disclaimer, the term of this patent is extended or adjusted under 35 U.S.C. 154(b) by 63 days.

(21) Appl. No.: 17/589,275

(22) Filed: Jan. 31, 2022

Related U.S. Application Data

(62) Division of application No. 15/295,219, filed on Oct. 17, 2016, now Pat. No. 11,234,768.

(60) Provisional application No. 62/242,276, filed on Oct. 15, 2015.

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 2090/376* (2016.02)

(58) Field of Classification Search
CPC ... A61B 17/17; A61B 17/1721; A61B 17/746; A61B 2090/067; A61B 2090/376; A61B 34/20; A61B 5/1071; A61B 5/1122; A61B 5/1127; A61B 5/4528; A61B 5/4571; A61B 5/686; A61B 5/743; A61B 6/12; A61B 6/461; A61B 6/487; A61B 90/06; A61B 90/37

See application file for complete search history.

(56) References Cited

U.S. PATENT DOCUMENTS

| | | | |
|---|---|---|---|
| 4,813,149 | A | 3/1989 | Herkimer |
| 5,030,222 | A | 7/1991 | Calandruccio |
| 5,700,268 | A | 12/1997 | Bertin |
| 5,808,665 | A | 9/1998 | Green |
| 6,036,696 | A | 3/2000 | Lambrecht |
| 6,246,200 | B1 | 6/2001 | Blumenkranz |
| 6,475,168 | B1 | 11/2002 | Pugsley |
| 6,799,380 | B2 | 10/2004 | Afriat |
| 7,083,624 | B2 | 8/2006 | Irving |
| 7,406,775 | B2 | 8/2008 | Funk |
| 7,674,264 | B2 | 3/2010 | Feiler |
| 7,763,027 | B2 | 7/2010 | Irving |
| 8,057,479 | B2 | 11/2011 | Stone |
| 8,337,507 | B2 | 12/2012 | Lang |

(Continued)

*Primary Examiner* — Samuel S Hanna
(74) *Attorney, Agent, or Firm* — Loginov & Associates, PLLC; William A. Loginov

(57) ABSTRACT

A template that includes a support structure pivotably mounted to a guide, wherein the guide includes a compass with angle markings, a first guide member extending from the vertex of the compass, a second guide member extending from the vertex of the compass. In another embodiment, a medical imaging system can include a medical imaging machine with a display screen, a support structure affixed to the medical imaging machine, and a guide pivotably mounted to the support structure. A method of aligning medical implants with anatomical structures includes positioning a template over the display screen, and comparing an angle of a medical tool or implant relative to the anatomical structure of the patient to a reference angle on the guide and installing the implant in the patient at the angle indicated by the guide.

5 Claims, 4 Drawing Sheets

(56) References Cited

U.S. PATENT DOCUMENTS

| | | |
|---|---|---|
| 8,382,758 B1 | 2/2013 | Sommers |
| 8,611,697 B2 | 12/2013 | Nathaniel |
| 8,782,914 B1 | 7/2014 | Deluca |
| 8,795,287 B2 | 8/2014 | Fritzinger |
| 8,864,768 B2 | 10/2014 | Hanson |
| 2002/0124426 A1 | 9/2002 | Dewberry |
| 2004/0147926 A1* | 7/2004 | Iversen .................. A61B 34/20 606/53 |
| 2004/0178312 A1 | 9/2004 | Parsons |
| 2006/0235420 A1 | 10/2006 | Irving |
| 2008/0027312 A1 | 1/2008 | Dick |
| 2008/0287959 A1 | 11/2008 | Quest |
| 2009/0053685 A1 | 2/2009 | Common |
| 2009/0248044 A1 | 10/2009 | Amiot |
| 2010/0049493 A1 | 2/2010 | Haimerl |
| 2014/0163563 A1 | 6/2014 | Reynolds |
| 2014/0163570 A1 | 6/2014 | Reynolds |
| 2016/0091117 A1 | 3/2016 | Boccoleri |

* cited by examiner

SCREEN-MOUNTED TRAJECTORY AND AIMING GUIDE FOR USE WITH FLUOROSCOPY

RELATED APPLICATIONS

This application is a divisional of co-pending U.S. patent application Ser. No. 15/295,219, entitled SCREEN-MOUNTED TRAJECTORY AND AIMING GUIDE FOR USE WITH FLUOROSCOPY, filed Oct. 17, 2016, which claims the benefit of U.S. Provisional Application Ser. No. 62/242,276, filed Oct. 15, 2015, entitled SCREEN-MOUNTED TRAJECTORY AND AIMING GUIDE FOR USE WITH MEDICAL IMAGING, the entire disclosure of which is herein incorporated by reference.

FIELD OF THE DISCLOSURE

This disclosure is in the field of medical devices, and more particularly devices for aiming objects inserted into the body using medical imaging.

BACKGROUND OF THE DISCLOSURE

Medial imaging is used for determining the alignment and placement of invasive medical implants (for example, surgical screws) that are inserted into a body. Fluoroscopy is one form of medical imaging used as a significant tool in these orthopedic procedures. Fluoroscopes use x-ray emissions to obtain images of the placement and movement of anatomical structures such as bones, and other radiopaque objects such as medical tools, screws, plates, and other implants.

FIG. 1 shows one example of medical imaging equipment known as a fluoroscope. A patient is positioned on the patent support 102. X-rays are then emitted from the x-ray tube 104. The x-rays travel through the patient and are received by an image receptor 106. Display screen 108 can show video of the real-time x-ray images. Radiopaque items such as bones and metal objects appear in the x-ray images displayed on display screen 108.

FIG. 2 shows one example of an x-ray image of an implant, as it might be seen through a fluoroscopy display screen. A human femur 202 is shown with an implant 204 in place. The implant 204 consists of a support plate 206, support plate screws 208, and a compression hip screw 210 used to repair a broken femoral head 212. Proper alignment and placement of implants reduces adverse outcomes and complications for the patient. The ultimate goal of joint surgery is to repair or replace a non-functional joint with a joint that functions as naturally as possible. Poor placement can result in harm to adjacent organs or tissues (for example, nerves and blood vessels), discomfort, gait problems, degradation of the prostheses and possible revision surgery.

Fluoroscopic checks during surgery give the surgeon an opportunity to properly align and place the implants. This is of particular importance for the proper trajectory of screws such as a compression screw 210. A surgeon who is able to quickly make a correct determination of alignment and seating of the implants leads to a shorter surgical time, which can result in a reduced tourniquet time, reduced anesthesia time, lower blood loss, and improved recovery by the patient. Implant penetration depth can be ascertained. Furthermore, frequent fluoroscopic checks increases the amount of ambient ionized radiation in the operating room, which can pose a long-term health risk for the patient and surgical team. Improvements in vision technology and shielded garments can reduce the amount of radiation, but not all of the risks of exposure.

It would be desirable to have an alignment system for properly aligning the surgical implants as quickly as possible, resulting in a better outcome for the patient and less exposure to radiation for the surgical team.

SUMMARY OF THE INVENTION

This present disclosure overcomes disadvantages of the prior art by providing an apparatus, system, and method for properly aligning a surgical implant quickly, resulting in a better outcome for the patient and less exposure to radiation for the surgical team. For this purpose, the system and method in an illustrative embodiment is in the form of a template that can overlay a fluoroscopy screen. The template can include a support structure and a guide. The guide can include a plurality of guide members and a compass with angle markings enabling a surgeon to quickly determine the angle of an implant relative to an anatomical structure.

In accordance with an embodiment, there is provided a template that includes a guide and a support structure pivotably mounted to the guide. The guide can include a compass with angle markings, a first guide member extending from the vertex of the compass, and a second guide member extending from the vertex of the compass.

The first guide member can be pivotably mounted at the vertex of the compass. The second guide member can also be pivotably mounted at the vertex of the compass. The support structure can be comprised of a support arm, with the support arm pivotably mounted to the first guide member at one end region of the support arm, and an anchoring base which can be pivotably mounted to the other end region of the support arm. The support arm can also be comprised of a plurality of telescoping extenders so that the support arm is extendable. The support structure can be comprised of a plurality of support arms, with the distal end region of one support arm pivotably mounted to the proximal end region of a second support arm, and an anchoring base pivotably mounted to the distal end region of the second support arm. The support structure can be comprised of an anchoring base and at least two support arms, with the support arms including pivotal mounts at proximal and distal end regions, with the first support arm pivotably mounted to the first guide member at a proximal end region of the first support arm, and at least one successive support arm pivotably mounted at its proximal end region to the distal end region of a previous support arm so that multiple support arms are linked together at their end regions, and an anchoring base is pivotably mounted to the distal end of the last support arm. The support structure can be comprised of a number of support arms comprised of pivotal mounts at proximal and distal end regions of the support arms, with the support arms linked together with a pivotal joint between successive support arms, with the first guide member pivotably mounted at a proximal end region of a first support arm, and an anchoring base pivotably mounted at a distal end region of the terminal support arm. The support structure can include an anchoring base that can be a suction cup, a clamp, an adhesive, or a sticky elastomer. The first and second guide members can be substantially transparent, and at least one guide mark can appear on each of the guide members. The guide marks can be adapted to align with at least one bone and at least one implant. The first and second guide members can be defined by an outer boundary, with the first and second guide members each comprised of at least one marker extending inwards from the outer boundary. The template can be further comprised of a medical imaging machine having a display screen, where the support structure can be affixed to the medical imaging machine so that the compass overlays the display screen. The template can be further comprised of a second compass pivotably mounted to the second guide member and a third guide member pivotably mounted to the second compass. The support structure can be pivotably mounted to the first guide member or the second guide member of the guide. The support structure can be pivotably mounted to the compass of the guide.

In accordance with another embodiment, there is provided a medical imaging system that can be comprised of a medical imaging machine having a display screen for displaying the image obtained by the medical imaging machine, a support structure affixed to the medical imaging machine, and a guide pivotably mounted to the support structure. The guide can be comprised of a compass with angle markings, and first and second guide members. The first and second guide members can extend from the vertex of the compass.

In accordance with an embodiment, a method of aligning medical implants with anatomical structures within a body is provided. The method can be comprised of positioning a template over an image of at least a portion of an anatomical structure of a patient appearing on a display screen of a medical imaging machine, where the template can include a guide and a support structure. The guide can include a compass with angle markings and a plurality of guide members extending from the vertex of the compass. The method can be further comprised of comparing an angle of a medical tool or implant relative to the anatomical structure of the patent to a reference angle by observing the medical tool or implant and the anatomical structure of the patent on the display screen and comparing the angle of the medical tool or implant relative to the anatomical structure of the patient to the reference angle of the template positioned over the image of the anatomical structure of the patient, and installing the implant in the patient at the angle indicated by the template.

The method can be further comprised of angularly rotating at least one of the guide members around the compass to set the guide at a desired angle. The method can be further comprised of angularly rotating at least one of the guide members around the compass to measure the angle of the medical tool or implant relative to the anatomical structure of the patent.

BRIEF DESCRIPTION OF THE DRAWINGS

The invention description below refers to the accompanying drawings, of which.

DETAILED DESCRIPTION

Figure 1:
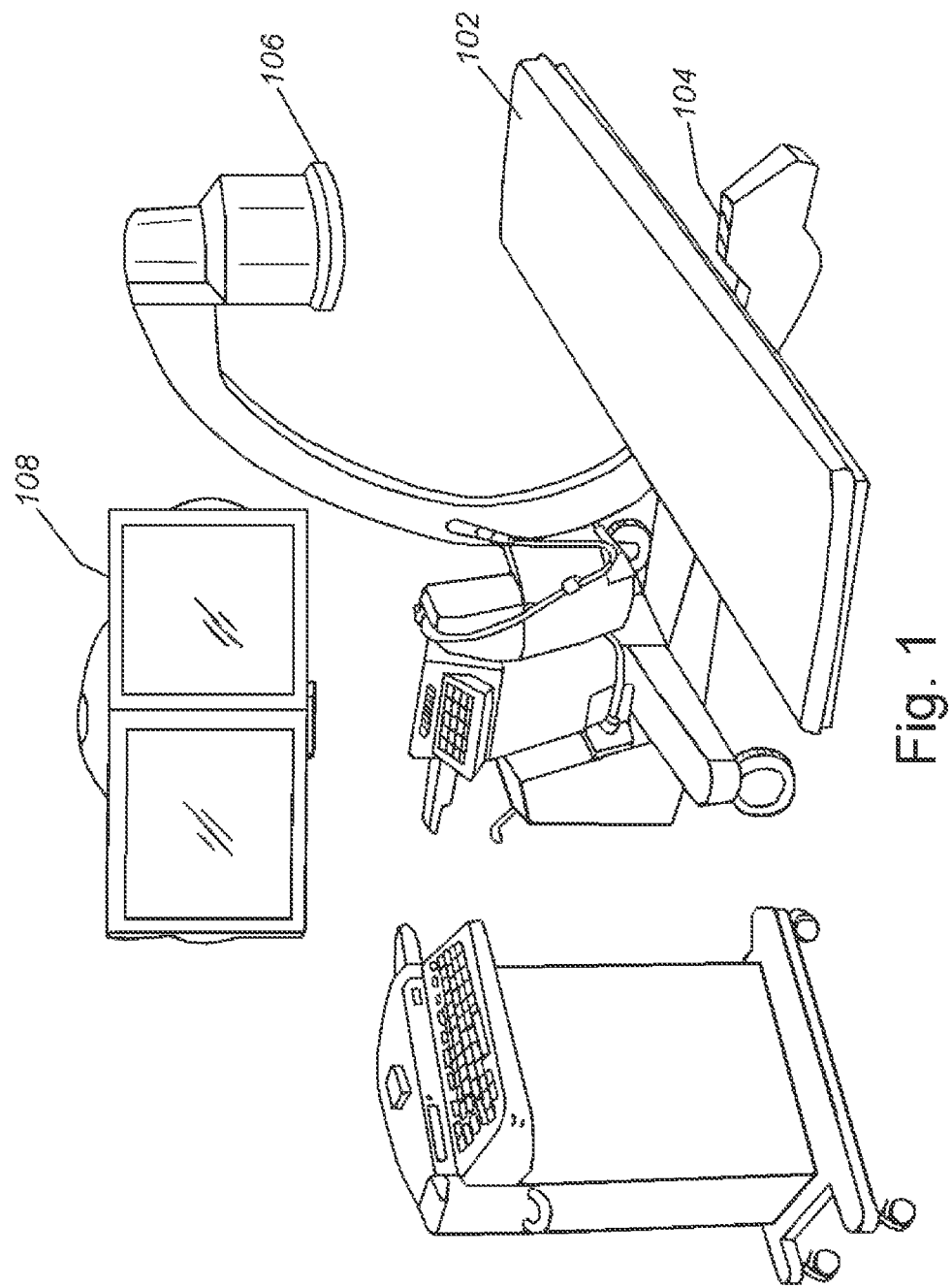
FIG. 1, already described, is a perspective view of a fluoroscopy machine in accordance with the conventional art.
Figure 2:
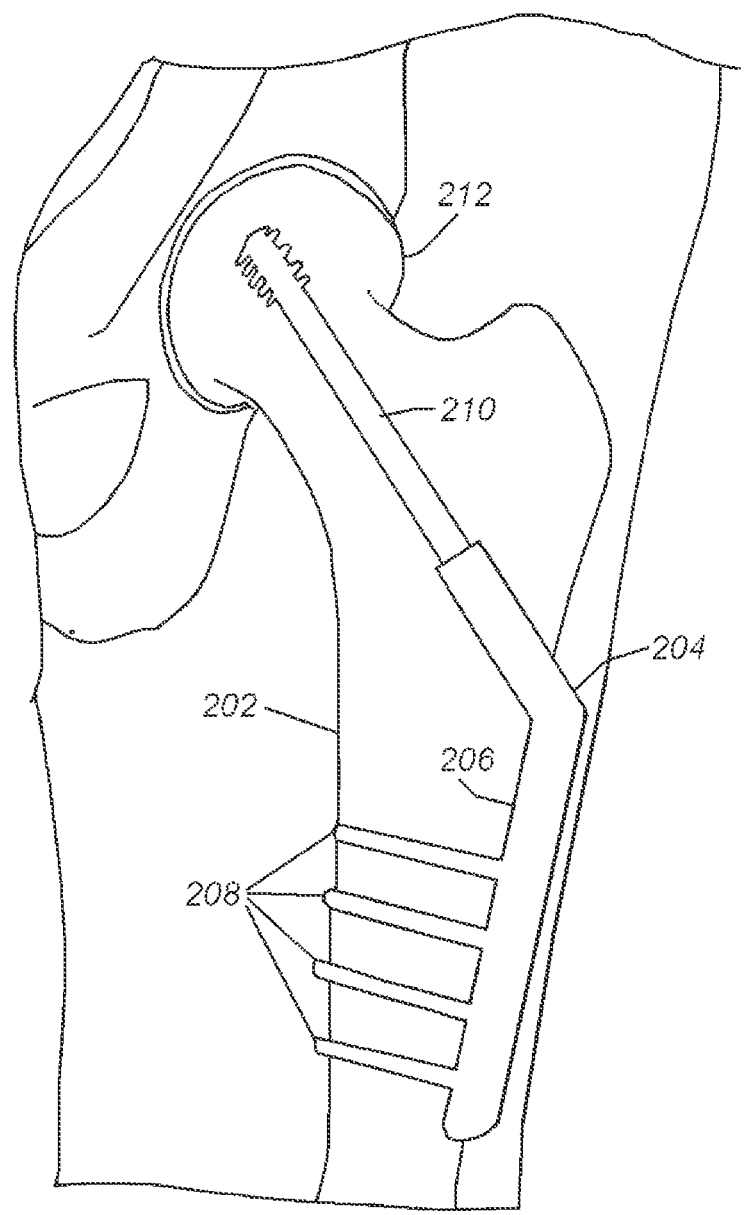
FIG. 2, already described, is a partial perspective view of a human anatomical structure with implants, as seen through a medical imaging display such as fluoroscopy.
Figure 3:
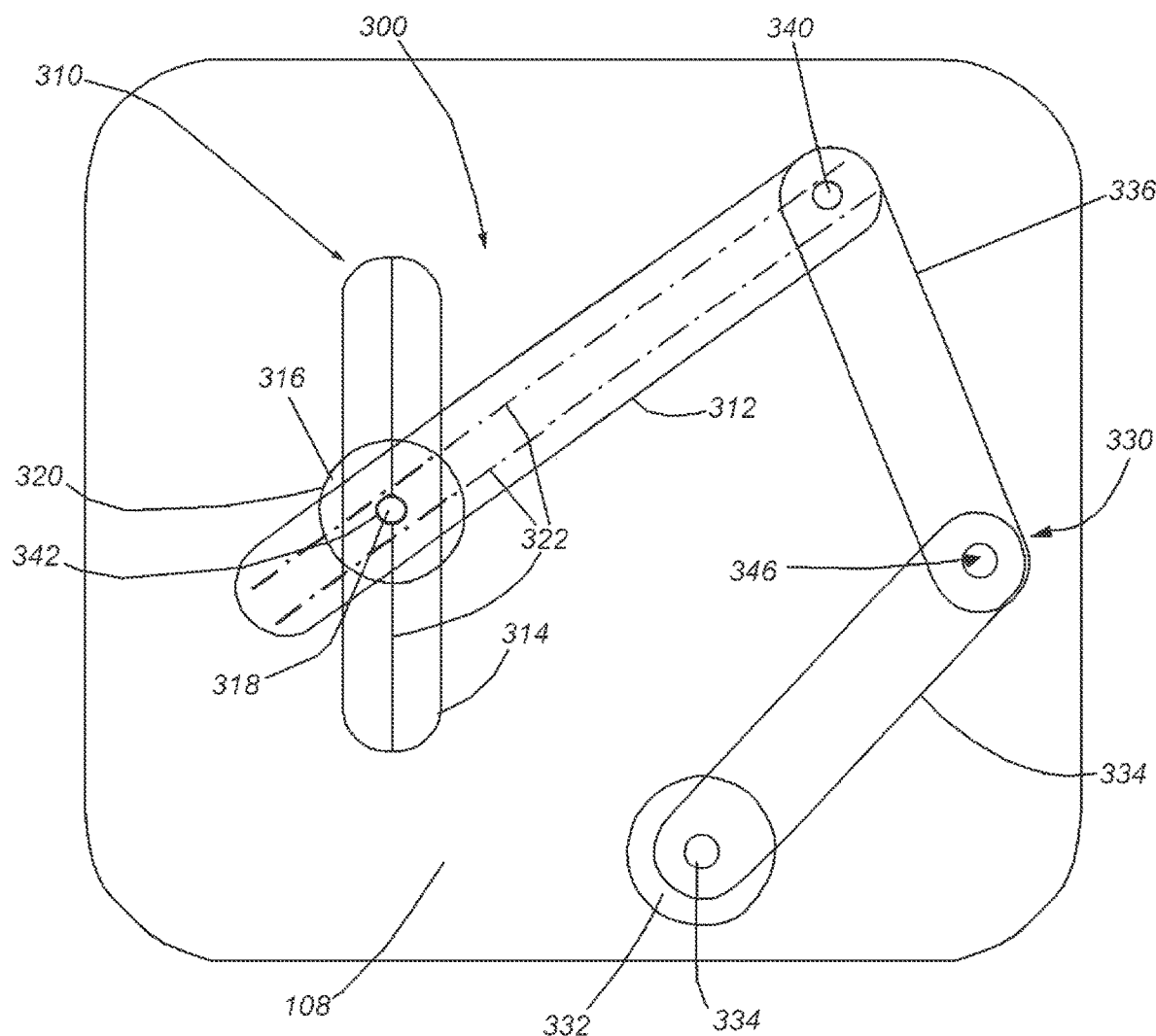
FIG. 3 is a perspective view of a screen-overlaid trajectory and aiming guide template for use with medical imaging.

FIG. 3 depicts an exemplary trajectory and aiming guide template 300 for use with medical imaging, such as fluoroscopy, installed over a display screen 108. The template can have a guide 310 and a support structure 330. The guide 310 can be pivotably mounted to the support structure 330 at a guide pivot 340. The guide 310 can have two guide members 312 and 314, and a compass 316. The compass 316 can have a vertex 318 and angle markings 320. The two guide members, 312 and 314, can extend from the vertex 318 of the compass 316. One or both of the guide members may be pivotably mounted on the vertex 318 at a vertex pivot 342 One or both of the guide members can pivot at the vertex 318 so that the angle formed by the two guide members can be measured using the angle markings 320 on the compass 316 as a protractor. In an embodiment, the guide members 312 and 314 can be sufficiently transparent to allow an anatomical structure to be seen through the guide members 312 and 314 on the display screen 108. The guide members 312 and 314 can have one or more guide marks 322 such as lines, dashes, or hash marks that can be used to align the guide members over an image of the anatomical structures and the trajectory of a compression screw 202. The guide marks 322 can also be used to measure the trajectory angle using the angle markings 320. Alternately, the guide members can be opaque, with one edge of the guide member defined by a vector projecting from the vertex. In another embodiment, the guide members can be defined by rigid outer perimeters with inwardly projecting rigid markers, or other possible embodiments allowing the user to view items on the display screen and use the template to measure the angles between them. The first guide member 312 can be pivotably mounted to the support structure 330 at the guide pivot 340. In alternate embodiments, the second guide member 314 or the compass 316 can be pivotably mounted to the support structure 330 at the guide pivot 340.

In an embodiment, the support structure 330 can have an anchoring base 332, and two support arms 334 and 336. The first support arm 334 can be pivotably mounted on the anchoring base 332 at an anchor pivot 344, and the second support arm 336 may be pivotably mounted on the first support arm 334 at a support pivoting 346. Other embodiments of support structures are considered, including a single, telescoping and pivoting support arm or more than two pivoting support arms. The anchoring base 332 may have one or more suction cups, clamps, sticky elastomers, adhesives, or other means of fixing the template over the display screen, and may include at least one support arm.

Figure 4:
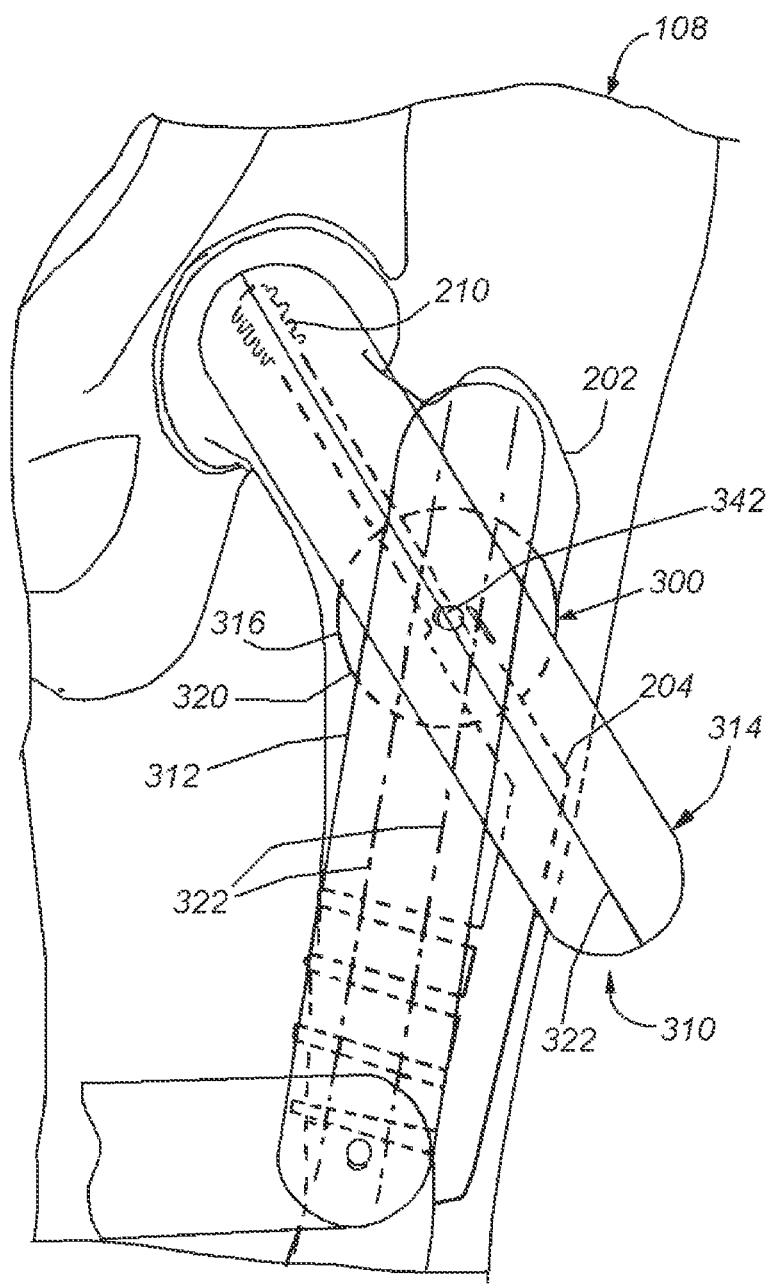
FIG. 4 is a partial perspective view of a trajectory and aiming guide template overlaid on a medical image display screen displaying a human anatomical structure receiving an implant.

As shown in FIG. 4, the template 300 can be positioned over a display screen such as a fluoroscopy screen 108 displaying an anatomical structure such as a femur 202 that will receive an implant 204. The guide 310 can be positioned over an image of the anatomical structure such as the femur 202. One guide member 312 may be positioned over the image of the anatomical structure such as a femur 202, and the other guide member 314 may be rotated on the vertex pivot 342 to the optimal trajectory angle for aiming a compression screw 210 for implanting. The trajectory angle of the compression screw 202 can be measured by using angle markings 320 to determine the angle between the two guide members 312 and 314. The guide marks 322 on the guide members 312 and 314 can be used to increase the accuracy of the placement of the guide members 312 and 314, and can be used to increase the accuracy of the angle measurement using the angle markings 320 on the compass 316. This allows the surgeon to see the anatomical structure, such as a femur 202, and a compression screw 210, and measure the angle between the femur 202 and the compression screw 210 using the compass 316 as a protractor, to ensure that the compression screw 210 is implanted at the optimal angle. The surgeon may set the optimal angle on the guide 310, and then install the compression screw 210 at the angle shown by the template, or the surgeon may prepare to install a compression screw 210 based on other factors such as the curvature of a bone or the location of fractures, and then use the guide 310 to measure the intended angle.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, embodiments herein can be practiced with guide members and the compass affixed to the display screen at the pivot point, without support arms. Alternatively, the embodiments herein can be practiced with more than two guide members for aligning multiple implants or screws. Or the embodiments herein can be practiced with a support arm affixed to the compass instead of to a guide member. Alternatively, the embodiments herein can be practiced with multiple compasses. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Accordingly, this description is meant to be taken only by way of example, and not to otherwise limit the scope of this invention.

What is claimed is:

1. A method of aligning medical implants with anatomical structures within a body comprising:

positioning a template over an image of at least a portion of an anatomical structure of a patient appearing on a display screen of a medical imaging machine, the template comprising a guide and a support structure, the guide including angle markings, the guide further comprising a plurality of guide members extending from a vertex;

comparing an angle of a medical tool or implant relative to the anatomical structure of the patient to a reference angle by observing the medical tool or implant and the anatomical structure of the patient on the display screen and comparing the angle of the medical tool or implant relative to the anatomical structure of the patient to the reference angle of the template positioned over the image of the anatomical structure of the patient; and installing the implant in the patient at the angle indicated by the template.

2. The method of claim 1, further comprising angularly rotating at least one of the guide members to set the guide at a desired angle.

3. The method of claim 1, further comprising angularly rotating at least one of the guide members to measure the angle of the medical tool or implant relative to the anatomical structure of the patient.

4. The method of claim 1 wherein the guide defines a compass with the angle markings.

5. The method as set forth in claim 1, further comprising engaging the display screen with an anchoring base of the guide using at least one of a suction cup, a clamp, an adhesive, and a sticky elastomer.

* * * * *